(12) United States Patent
Tseng et al.

(10) Patent No.: US 8,900,247 B2
(45) Date of Patent: Dec. 2, 2014

(54) MEASURING AND GUIDING DEVICE FOR RECONSTRUCTION SURGERY

(75) Inventors: Ching-Shiow Tseng, Jhongli (TW); Tien-Hsiang Wang, Jhongli (TW); Chi-Pin Huang, Jhongli (TW)

(73) Assignee: National Central University, Jhongli, Taoyuan County (TW)

( * ) Notice: Subject to any disclaimer, the term of this patent is extended or adjusted under 35 U.S.C. 154(b) by 97 days.

(21) Appl. No.: 13/593,230

(22) Filed: Aug. 23, 2012

(65) Prior Publication Data

US 2013/0304075 A1    Nov. 14, 2013

(30) Foreign Application Priority Data

May 11, 2012  (TW) .............................. 101116868 A

(51) Int. Cl.
*A61B 17/90* (2006.01)
*A61B 17/15* (2006.01)
*A61B 17/58* (2006.01)

(52) U.S. Cl.
USPC .......................................... 606/102; 606/87

(58) Field of Classification Search
USPC ........... 606/53, 82, 86 R, 87, 88, 89, 90, 102, 606/105, 903, 904; 623/17.17–17.19; 403/90, 96, 97
See application file for complete search history.

(56) References Cited

U.S. PATENT DOCUMENTS

| | | | |
|---|---|---|---|
| 3,277,601 A * | 10/1966 | Ryan | 446/378 |
| 6,322,566 B1 * | 11/2001 | Minoretti et al. | 606/105 |
| 6,325,803 B1 * | 12/2001 | Schumacher et al. | 606/71 |
| 7,008,432 B2 * | 3/2006 | Schlapfer et al. | 606/90 |
| 8,474,677 B2 * | 7/2013 | Woodard et al. | 227/176.1 |
| 8,529,571 B2 * | 9/2013 | Horan et al. | 606/87 |
| 8,632,541 B2 * | 1/2014 | Bigazzi et al. | 606/54 |
| 8,646,365 B2 * | 2/2014 | Hsieh | 81/177.8 |
| 8,657,830 B2 * | 2/2014 | Sarin et al. | 606/91 |
| 8,657,880 B2 * | 2/2014 | Paulos | 623/13.13 |
| 8,685,036 B2 * | 4/2014 | Jones et al. | 606/102 |
| 2004/0068263 A1 * | 4/2004 | Chouinard et al. | 606/86 |
| 2006/0058791 A1 * | 3/2006 | Broman et al. | 606/61 |
| 2007/0049936 A1 * | 3/2007 | Colleran et al. | 606/61 |
| 2010/0168797 A1 * | 7/2010 | Graf | 606/264 |
| 2010/0191243 A1 * | 7/2010 | Horan et al. | 606/87 |
| 2010/0260543 A1 * | 10/2010 | Cameron et al. | 403/355 |
| 2011/0040331 A1 * | 2/2011 | Fernandez et al. | 606/264 |
| 2014/0012269 A1 * | 1/2014 | Bass | 606/90 |
| 2014/0084761 A1 * | 3/2014 | Scott et al. | 312/209 |
| 2014/0100619 A1 * | 4/2014 | DiPaola | 606/86 R |
| 2014/0107656 A1 * | 4/2014 | Masson et al. | 606/90 |
| 2014/0114369 A1 * | 4/2014 | Hanson et al. | 606/86 R |

* cited by examiner

*Primary Examiner* — Michael T Schaper
*Assistant Examiner* — Amy Sipp
(74) *Attorney, Agent, or Firm* — Juan Carlos A. Marquez; Bacon & Thomas PLLC

(57) ABSTRACT

The present invention discloses a measuring and guiding device for reconstruction surgery. The measuring and guiding device includes: a pair of rotary aims, a connector, and a pair of fixators. Each rotary arm includes: a first shaft, a first joint body and a second joint body. The pair of rotary arms is joined together by extending through each of the first joint bodies using the connector. Besides, each fixator includes: a second shaft, a third joint body and a guiding portion, and each third joint body is connected with one of the second joint bodies. With the implementation of the present invention, the measuring and guiding device is capable of measuring an operating site and guiding the operation precisely during reconstruction surgery.

6 Claims, 10 Drawing Sheets

US 8,900,247 B2

MEASURING AND GUIDING DEVICE FOR RECONSTRUCTION SURGERY

This application claims priority to Taiwan R.O.C. Patent Application No. 101116868, which was filed on May 11, 2012, and which is hereby incorporated in its entirety by reference.

BACKGROUND OF THE INVENTION

1. Technical Field

The present invention relates to a measuring and guiding device for reconstruction surgery, and more particularly, to a measuring and guiding device for mandible reconstruction surgery.

2. Description of Related Art

Among facial bones, the mandible has dual functions of aesthetics and mastication. Fracture caused due to traffic accidents or invasion of tumors is the most common reason that the mandible has to be resected. No matter which kind of factor causes resection of the mandible, patients must be subjected to plastic surgery. Therefore, the defective site caused by the resection operation must be reconstructed in different operating ways according to the patients' conditions.

Because the fibula of a leg bears only 15% of the weight of the overall body, resection of the fibula has a slight influence on the human body. Thus, the current reconstruction method is to resect the fibula to fill the site where the mandible has been resected. According to the technologies currently available, computer models of the mandible and the fibula are produced firstly, on which precut ranges of the mandible and the fibula are determined; and then, by using the rapid prototyping technology, a cutting template is produced to provide planning and reference for cutting of the fibula. However, the production cost of the cutting template is too high, and the cutting template must be custom made according to individual cases and cannot be reused.

Furthermore, the way of making a plan using the computer models may sometimes cause that the conditions in the operation become a little different from those in the plan because of misjudging the tumor size, and consequently, accurate measurement and cutting guidance cannot be achieved instantly according to real operation conditions. Accordingly, it is desired to develop a surgical instrument that is reusable and can measure the defective site of a patient's mandible and precisely guide the cutting position of the fibula during surgery.

SUMMARY OF THE INVENTION

The present invention provides a measuring and guiding device for reconstruction surgery, which comprises a pair of rotary arms, a connector and a pair of fixators. The primary objective of the present invention is to measure a defective site and to guide the resection operation precisely during the reconstruction surgery.

The present invention provides a measuring and guiding device for reconstruction surgery, comprising: a pair of rotary arms, each of the rotary arms comprising: a first shaft, having a first end portion and a second end portion; a first joint body, being disposed at the first end portion; and a second joint body, being disposed at the second end portion; a connector, extending through each of the first joint bodies and connecting the pair of rotary arms together with an included angle being adjustable; and a pair of fixators, each of the fixators comprising: a second shaft, having a third end portion and a fourth end portion; a third joint body, being disposed at the third end portion and joined with one of the second joint bodies with an included angle being adjustable; and a guiding portion, being disposed at the fourth end portion.

With the implementation of the present invention, at least the following improvements can be achieved:

I. the defective site and the operating site can be measured precisely;

II. the cutting operation can be guided precisely;

III. the measuring and guiding device can be easily disassembled, cleaned, and sterilized;

IV. the measuring and guiding device features simple operation and can be used for any patients; and V. the measuring and guiding device can be reused after being sterilized.

Hereinafter, the detailed features and advantages of the present invention are described in detail by way of the preferred embodiments of the present invention so as to enable persons skilled in the art to gain insight into the technical disclosure of the present invention, implement the present invention accordingly, and readily understand the objectives and advantages of the present invention by making reference to the disclosure of the specification, the claims, and the drawings of the present invention.

DETAILED DESCRIPTION OF THE EMBODIMENTS OF THE INVENTION

Figure 1:
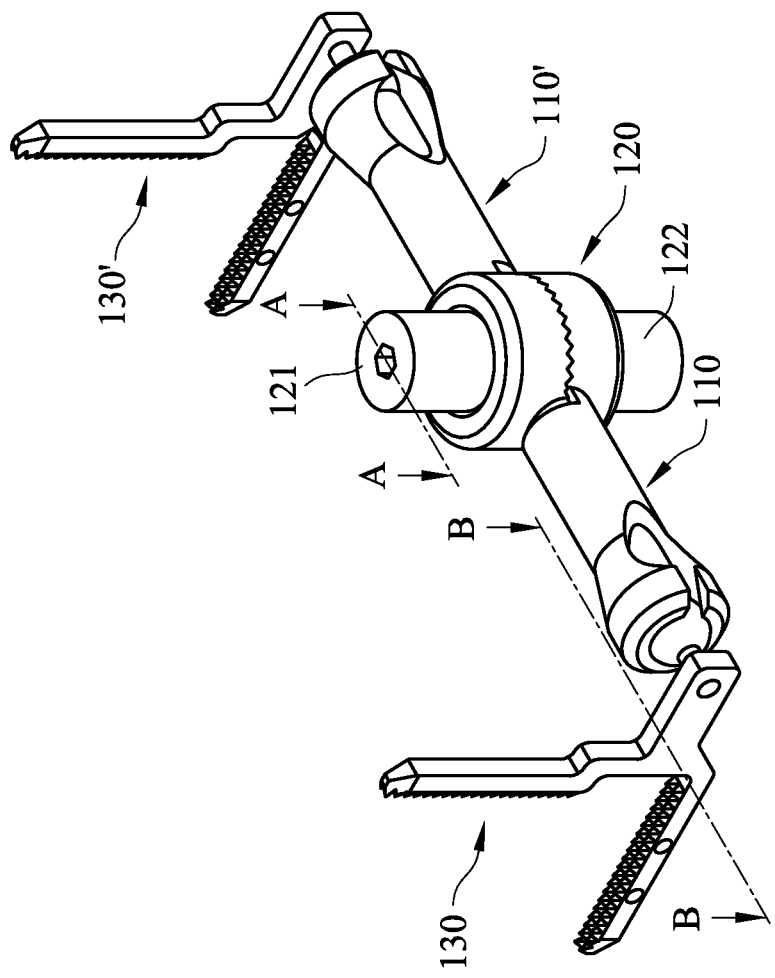
FIG. 1 is a perspective assembly view of a measuring and guiding device for reconstruction surgery according to an embodiment of the present invention.
Figure 2:
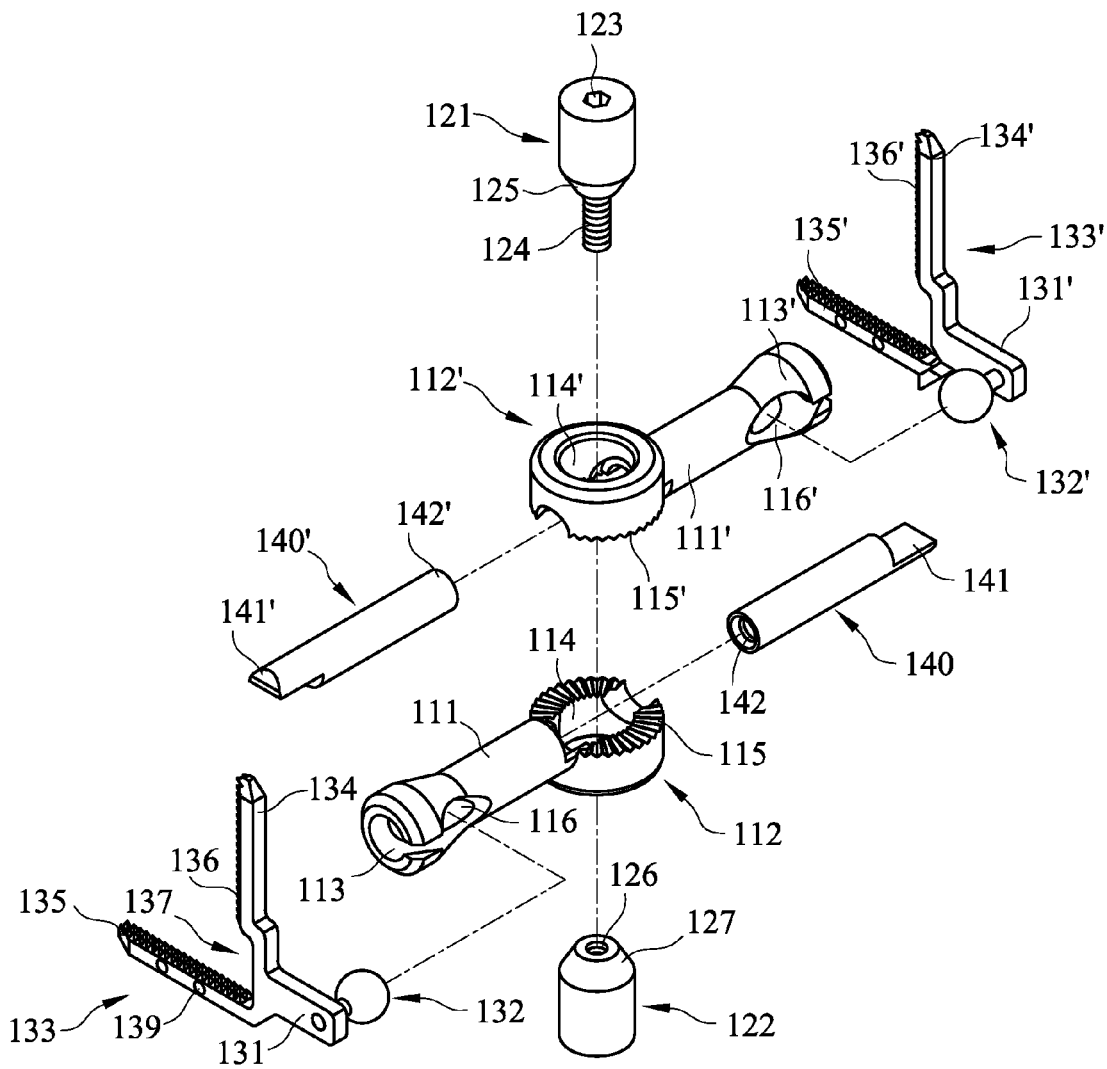
FIG. 2 is a perspective explosion view of the measuring and guiding device for reconstruction surgery according to an embodiment of the present invention.

As shown in FIG. 1 and FIG. 2, this embodiment is a measuring and guiding device 100 for reconstruction surgery, for example, for mandible reconstruction surgery. The measuring and guiding device 100 for reconstruction surgery comprises a pair of rotary arms 110, 110', a connector 120 and a pair of fixators 130, 130'. Each of the rotary arms 110, 110' comprises a first shaft 111, 111', a first joint body 112, 112' and a second joint body 113, 113'.

The pair of rotary arms 110, 110' is adapted to measure a length of a defective site or an operating site. A distance between two ends of the pair of rotary arms 110, 110' can be changed by changing an included angle between the pair of rotary arms 110, 110', so the length of the defective site or the operating site can be measured. For example, when the pair of rotary arms 110, 110' is used in the mandible reconstruction surgery, the length of the defective site of the mandible must be measured firstly, and the length of the operating site of the fibula that needs to be cut out is measured according to this fixed length.

Each of the first shafts 111, 111' has a first end portion and a second end portion. Each of the first joint bodies 112, 112' is disposed at the first end portion of the first shafts 111, 111' respectively and each of the rotary arms 110, 110' is connected with the connector 120 via a corresponding one of the first joint bodies 112, 112' thereof. Only when the two first joint bodies 112, 112' are fixedly connected with each other, the included angle between the pair of rotary arms 110, 110' can be thus fixed and the distance between the two ends of the pair of rotary arms 110, 110' can be determined to achieve the measuring purpose.

Figure 11:
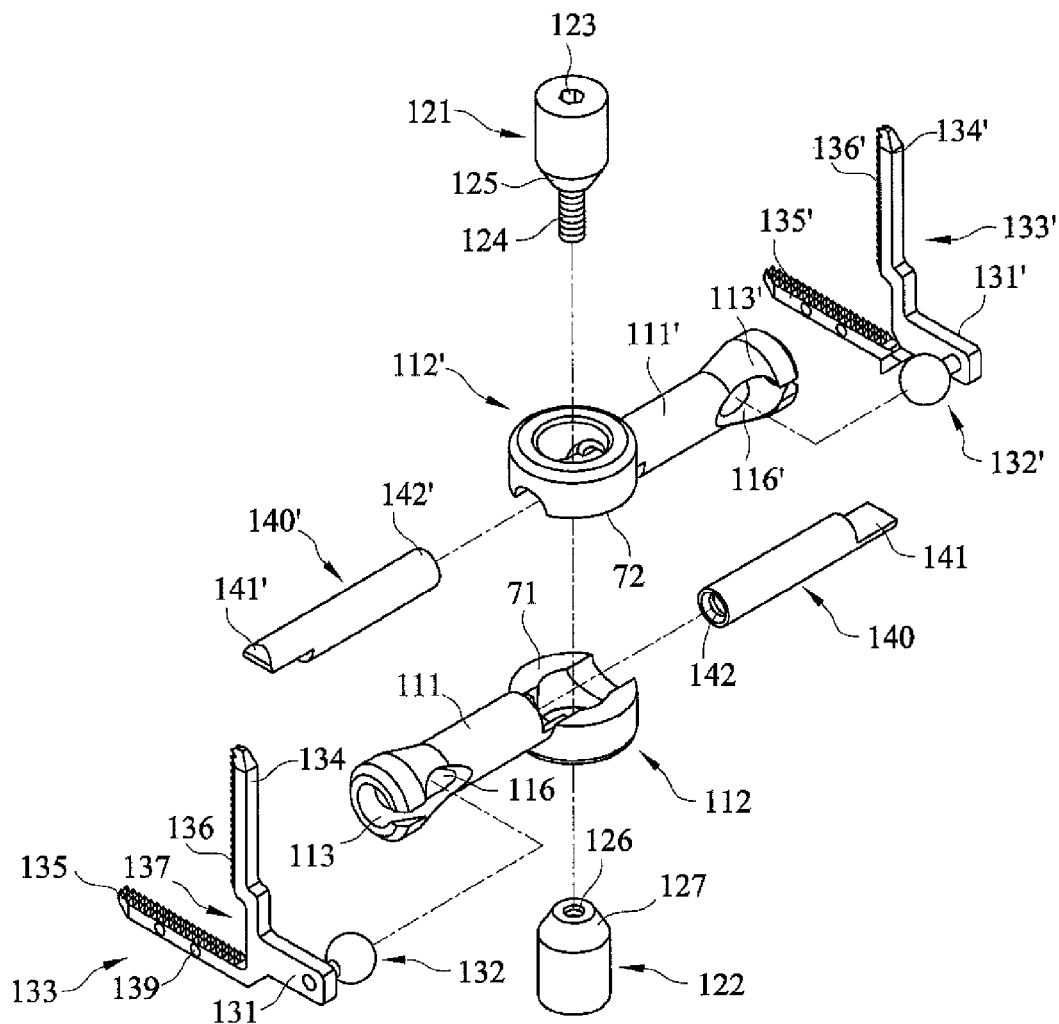
FIG. 11 is a perspective view of the measuring and guiding device for reconstruction surgery according to another embodiment of the present invention.

Therefore, each of the first joint bodies 112, 112' may be an annular structure 114, 114', and surfaces of the two annular structures 114, 114' that contact with each other are further formed with an engaging construction 115, 115' respectively. Engagement between the engaging constructions 115, 115' of the upper and the lower annular structures 114, 114' that contact with each other can make the two annular structures 114, 114' fixed with each other without rotation with respect to each other, and can thus fix the included angle between the pair of rotary arms 110, 110'. Furthermore, the surfaces of the two annular structures 114, 114' that contact with each other may also have a structure of an elastic material formed thereon, and the resistance caused by the structure of the elastic material can also prevent the surfaces of the upper and the lower annular structures 114, 114' that contact with each other from rotating with respect to each other and can thus fix the included angle between the pair of rotary arms 110, 110'. Also, as shown in FIG. 11, each of the first joint bodies 112, 112' may be a flat structure 114, 114', and an elastic washer may be further disposed between the two flat structures 114, 114'. The resistance caused by the elastic washer can also make the surfaces of the upper and the lower flat structures 114, 114' that contact with each other fixed with each other without rotation with respect to each other and can thus fix the included angle between the pair of rotary arms 110, 110'. Each of the second joint bodies 113, 113' is disposed at one of the second end portions, and each of the rotary arms 110, 110' is connected with one of the fixators 130, 130' via a corresponding one of the second joint bodies 113, 113' thereof.

Therefore, each of the first joint bodies 112, 112' may be an annular structure 114, 114', and surfaces of the two annular structures 114, 114' that contact with each other are further formed with an engaging construction 115, 115' respectively. Engagement between the engaging constructions 115, 115' of the upper and the lower annular structures 114, 114' that contact with each other can make the two annular structures 114, 114' fixed with each other without rotation with respect to each other, and can thus fix the included angle between the pair of rotary arms 110, 110'. Furthermore, the surfaces of the two annular structures 114, 114' that contact with each other may also have a structure of an elastic material formed thereon, and the resistance caused by the structure of the elastic material can also prevent the surfaces of the upper and the lower annular structures 114, 114' that contact with each other from rotating with respect to each other and can thus fix the included angle between the pair of rotary arms 110, 110'. Also, as shown in FIG. 11, each of the first joint bodies 112, 112' may be a flat structure 71, 72, and an elastic washer may be further disposed between the two flat structures 71, 72. The resistance caused by the elastic washer can also make the surfaces of the upper and the lower flat structures 71, 72 that contact with each other fixed with each other without rotation with respect to each other and can thus fix the included angle between the pair of rotary arms 110, 110'. Each of the second joint bodies 113, 113' is disposed at one of the second end portions, and each of the rotary arms 110, 110' is connected with one of the fixators 130, 130' via a corresponding one of the second joint bodies 113, 113' thereof.

The pair of fixators 130, 130' is adapted to fix the measuring and guiding device 100 for reconstruction surgery to the defective site or the operating site and guides the cutting direction and the cutting angle during the reconstruction surgery. Each of the fixators 130, 130' comprises a second shaft 131, 131', a third joint body 132, 132' and a guiding portion 133, 133'.

Figure 3:
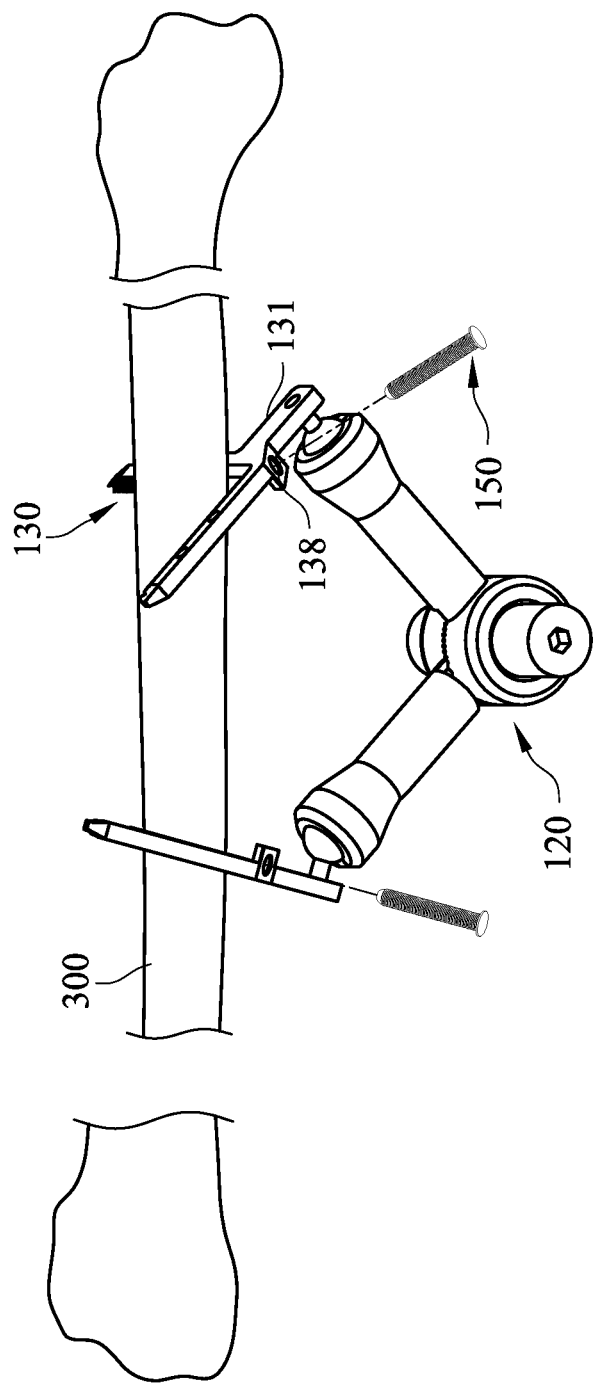
FIG. 3 is a schematic view I illustrating a guided cutting process according to an embodiment of the present invention.
Figure 4:
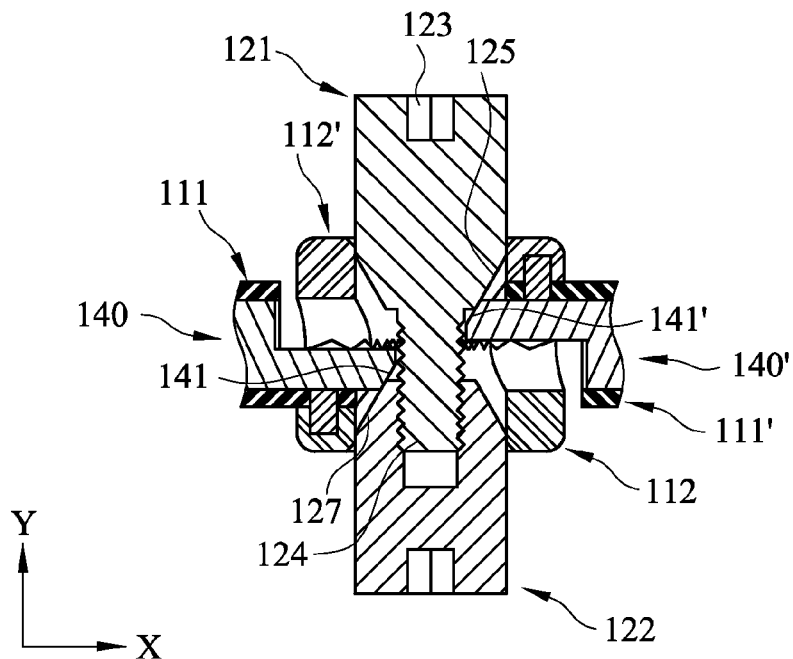
FIG. 4 is the cross-sectional view taken along a line A-A in FIG. 1.
Figure 5:
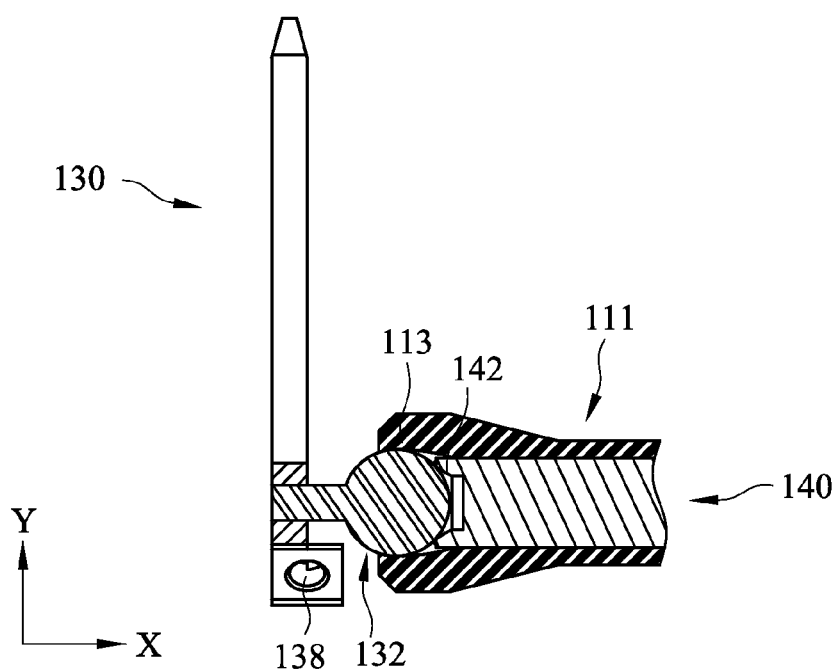
FIG. 5 is the cross-sectional view taken along a line B-B in FIG. 1.

Referring to FIG. 3 together, the second shaft 131 has a third end portion and a fourth end portion. The second shaft 131 may further have at least one first fixing guide hole 138 formed in a side surface thereof, and the at least one first fixing guide hole 138 may work with a screw 150 to fix the measuring and guiding device 100 for reconstruction surgery at the operating site (e.g., a fibula 300) more securely during the reconstruction surgery.

The third joint body 132 is disposed at the third end portion and joined with the second joint body 113 with an included angle being adjustable. Through adjustment of the angle between the third joint body 132 and the second joint body 113, a direction of a cutting plane of the defective site can be determined. When the third joint body 132 is of a spherical form, the second joint body 113 may be a spherical recess to allow the third joint body 132 to rotate in the second joint body 113 at various angles.

The guiding portion 133 is disposed at the fourth end portion to guide the cutting direction during the reconstruction surgery. During the mandible reconstruction surgery for example, at a cutting plane of the defective site of the inaudible, a direction of the cutting plane of the defective site is firstly determined through adjustment of the angle between the third joint body 132 and the second joint body 113, and this direction of the cutting plane is just a direction of a plane formed by the guiding portion 133; and the guiding portion 133 guides the cutting direction at the operating site (e.g., the fibula 300).

Each of the guiding portions 133, 133' may be an L-shaped plate, which may be divided into an L upper portion 134, 134' and an L lower portion 135, 135'. An angular space 137 formed by inner sides of the L-shaped plate that has an included angle may be used to snap-fit the guiding portion 133 onto the operating site (e.g., the fibula 300). The inner sides of the L-shaped plate that form an included angle may be formed with a sawtooth structure 160 respectively, and may also be formed with a tine structure 136, 136' or a skidproof structure respectively so that the guiding portion 133 can be snap-fitted onto the operating site (e.g., the fibula 300) more securely. Furthermore, each of the L-shaped plates may further have at least one second fixing guide hole 139 formed in a side surface thereof, which can be used to directly fix the guiding portion 133 to a side edge of the defective site for the measuring purpose.

Referring to FIGS. 1, 2 and 3, each of the guiding portions 133, 133' may be an L-shaped plate, which may be divided into an L upper portion 134, 134' and an L lower portion 135, 135'. An angular space 137 formed by inner sides of the L-shaped plate that has an included angle may be used to snap-fit the guiding portion 133 onto the operating site (e.g., the fibula 300). The inner sides of the L-shaped plate that form an included angle may be formed with a sawtooth structure 160 respectively, and may also be formed with a tine structure 136, 136' or a skidproof structure respectively so that the guiding portion 133 can be snap-fitted onto the operating site (e.g., the fibula 300) more securely. Furthermore, each of the L-shaped plates may further have at least one second fixing guide hole 139 formed in a side surface thereof, which can be used to directly fix the guiding portion 133 to a side edge of the defective site for the measuring purpose.

While the upper joint body 121 and the lower joint body 122 are locked, the upper bevel 125 of the upper joint body 121 or the lower bevel 127 of the lower joint body 122 presses against and contacts with a cross section of an end 141', 141 of the sliding shaft piece within the hollow portion 116', 116. Thus, the sliding shaft piece 140', 140 is pushed outwards from the upper joint body 121 and the lower joint body 122, and this drives the other end 142', 142 of the sliding shaft piece to press against and contact with the third joint body 132', 132 so that the third joint body 132', 132 connected to the second joint body 113', 113 can be fixed in the second joint body 113', 113. Therefore, while the upper joint body 121 and the lower joint body 122 are locked, all the joints of the measuring and guiding device 100 for reconstruction surgery are also completely fixed simultaneously.

Figure 6:
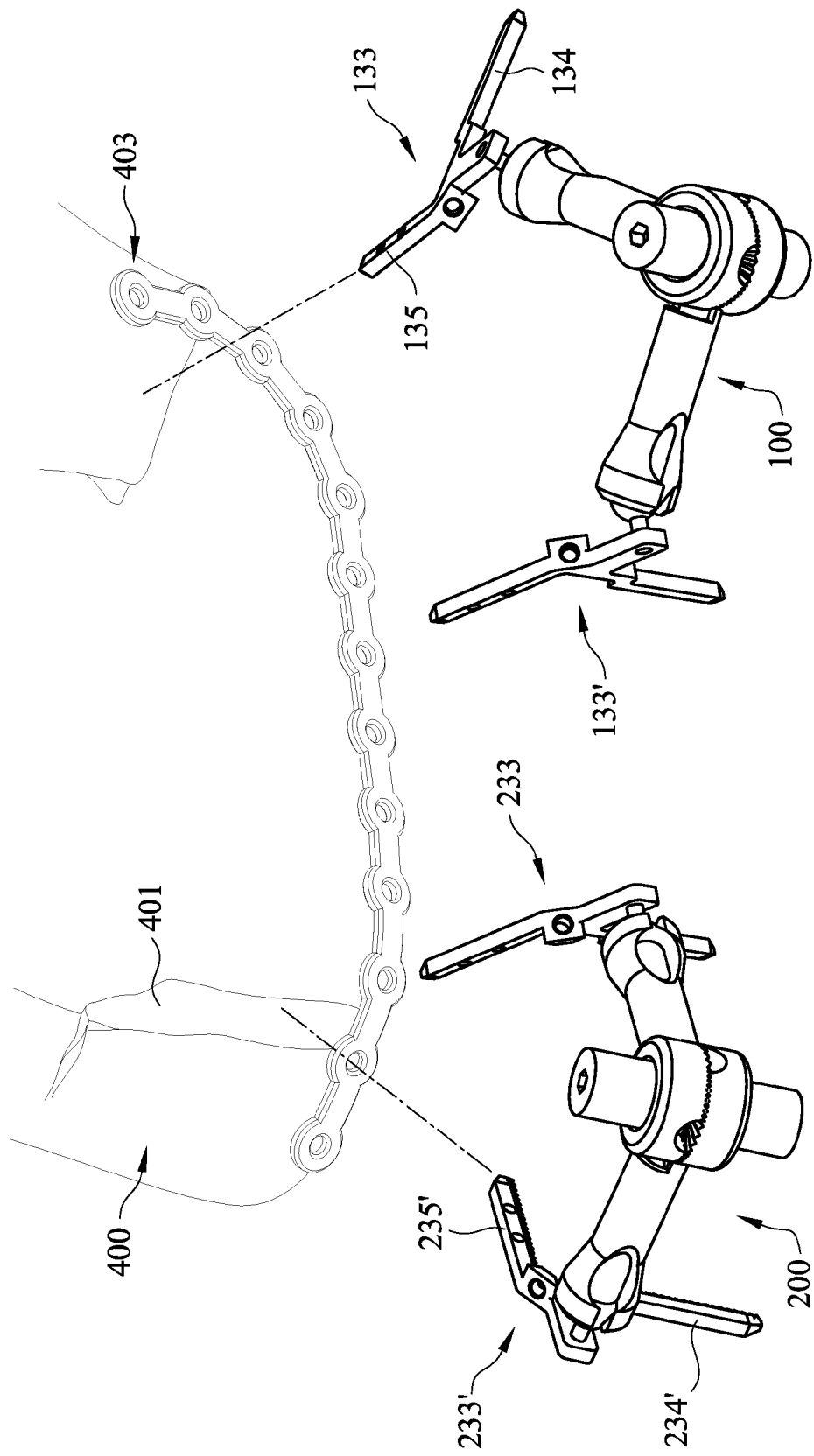
FIG. 6 is a schematic view I illustrating a measuring process according to an embodiment of the present invention.
Figure 7:
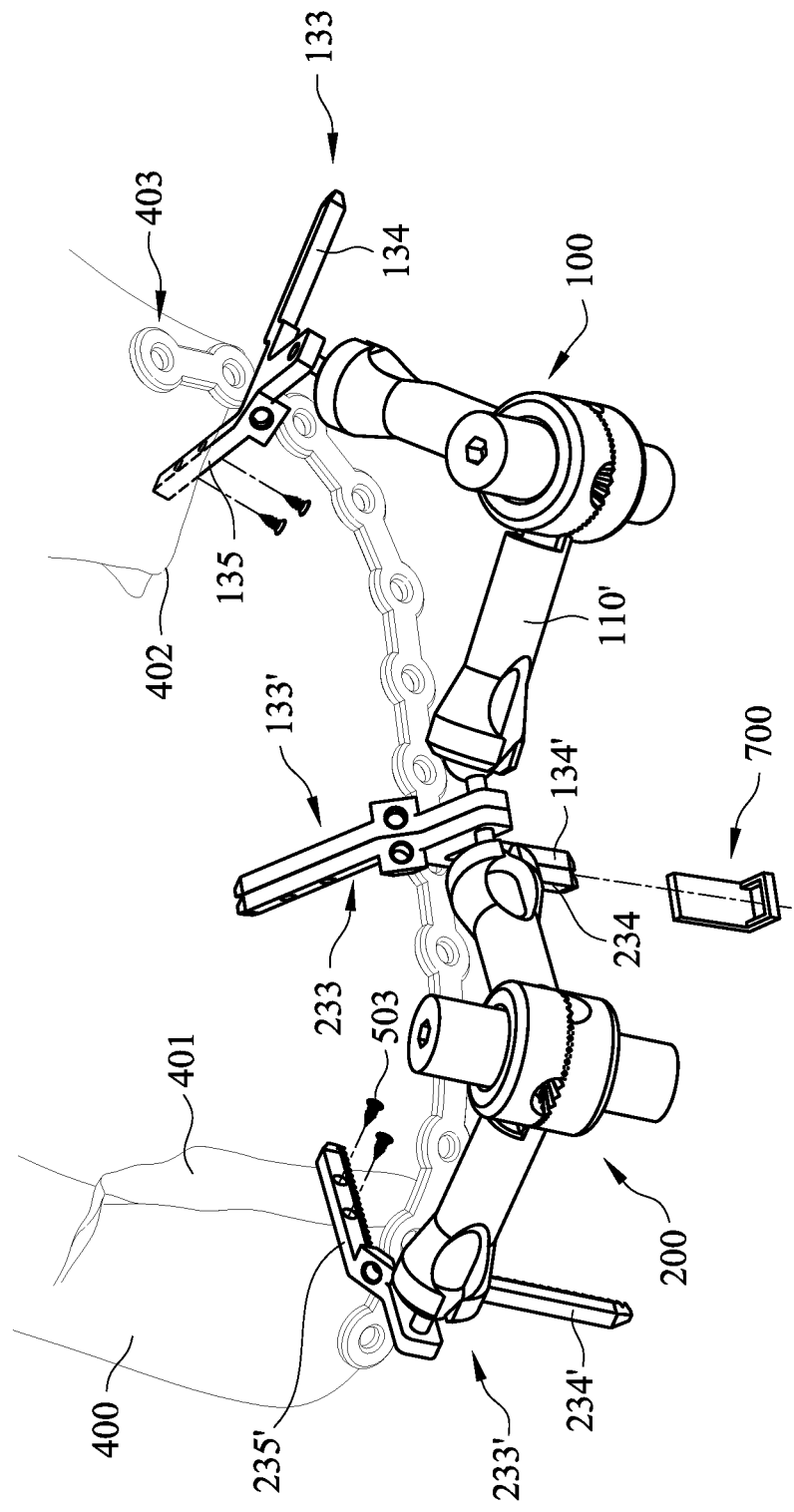
FIG. 7 is a schematic view II illustrating the measuring process according to an embodiment of the present invention.

As shown in FIG. 2, FIG. 6 and FIG. 7, mandible reconstruction surgery will be taken as an example. When the mandible is resected due to accidents or diseases, two defective side surfaces 401, 402 will be exposed from a defective site 400 (e.g., the mandible); and a bone plate 403 is fixed on the defective side 400, and the measuring and guiding device 100 for reconstruction surgery is hanged on the bone plate 403. When the length of the defective site 400 is larger than a length that can be measured by one measuring and guiding device 100 for reconstruction surgery, a second measuring and guiding device 200 for reconstruction surgery must be used in combination to measure the length of the defective site 400. For example, each of the guiding portions 233', 133 has second fixing guide holes 139 formed in the respective L lower portion 235', 135, and the guiding portions 233', 133 can be fixed to the defective side surfaces 401, 402 by using screws 503 through the second fixing guide holes 139. In this case, a plane formed by the L lower portion 235' and the L upper portion 234' is identical to the plane of the defective side surface 401, and a plane formed by the L lower portion 135 and the L upper portion 134 is identical to the plane of the defective side surface 402.

Figure 8:
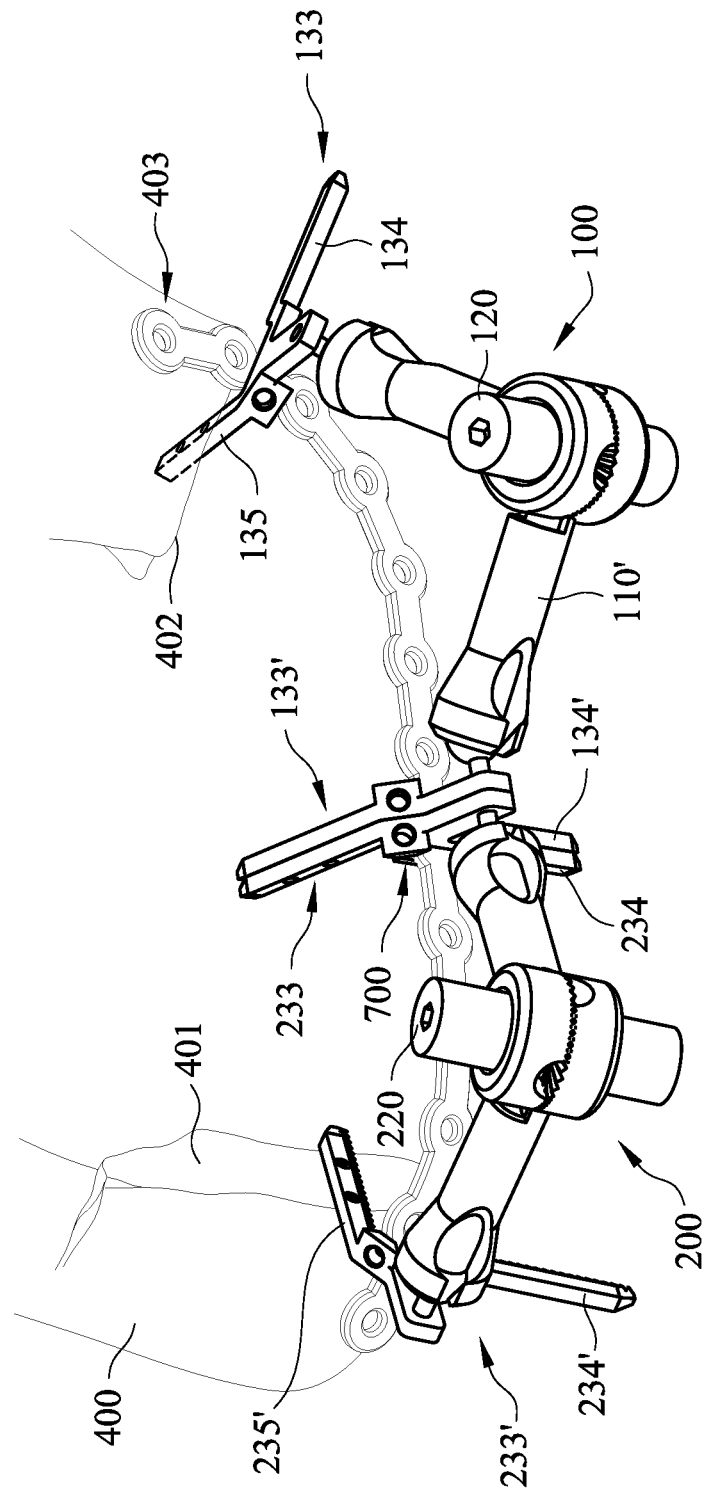
FIG. 8 is a schematic vu III illustrating the measuring process according to an embodiment of the present invention.

Referring to FIG. 8 together, after the two guiding portions 233', 133 at the side of the mandible are fixed, the two measuring and guiding devices 200, 100 for reconstruction surgery must be used simultaneously to measure the length of the defective site 400. Specifically, an appropriate length is obtained through adjustment by changing an included angle between the two rotary arms 110' until the two adjacent guiding portions 233, 133' can abut against each other; and then, the two adjacent L upper portions 234, 134' are tightened and fixed by using a joint ring 700. Finally, the connectors 220, 120 of the two measuring and guiding devices 200, 100 for reconstruction surgery are locked together, thus completing measurement of the defective site 400.

Figure 9:
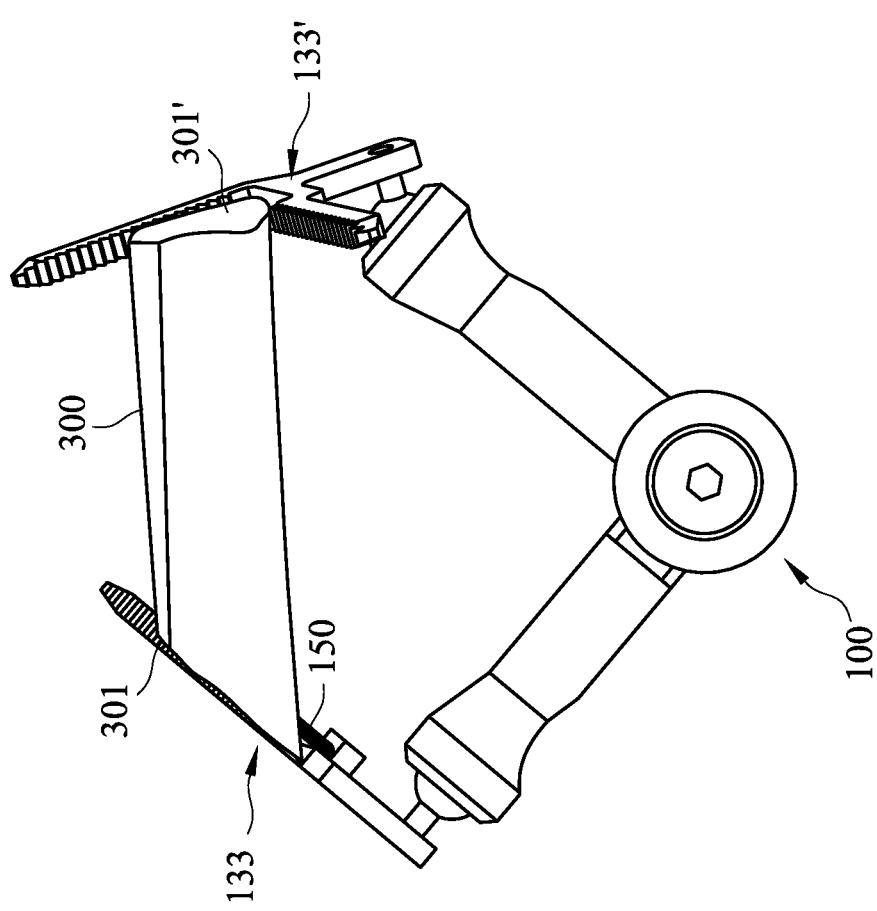
FIG. 9 is a schematic view II illustrating the guided cutting process according to an embodiment of the present invention.
Figure 10:
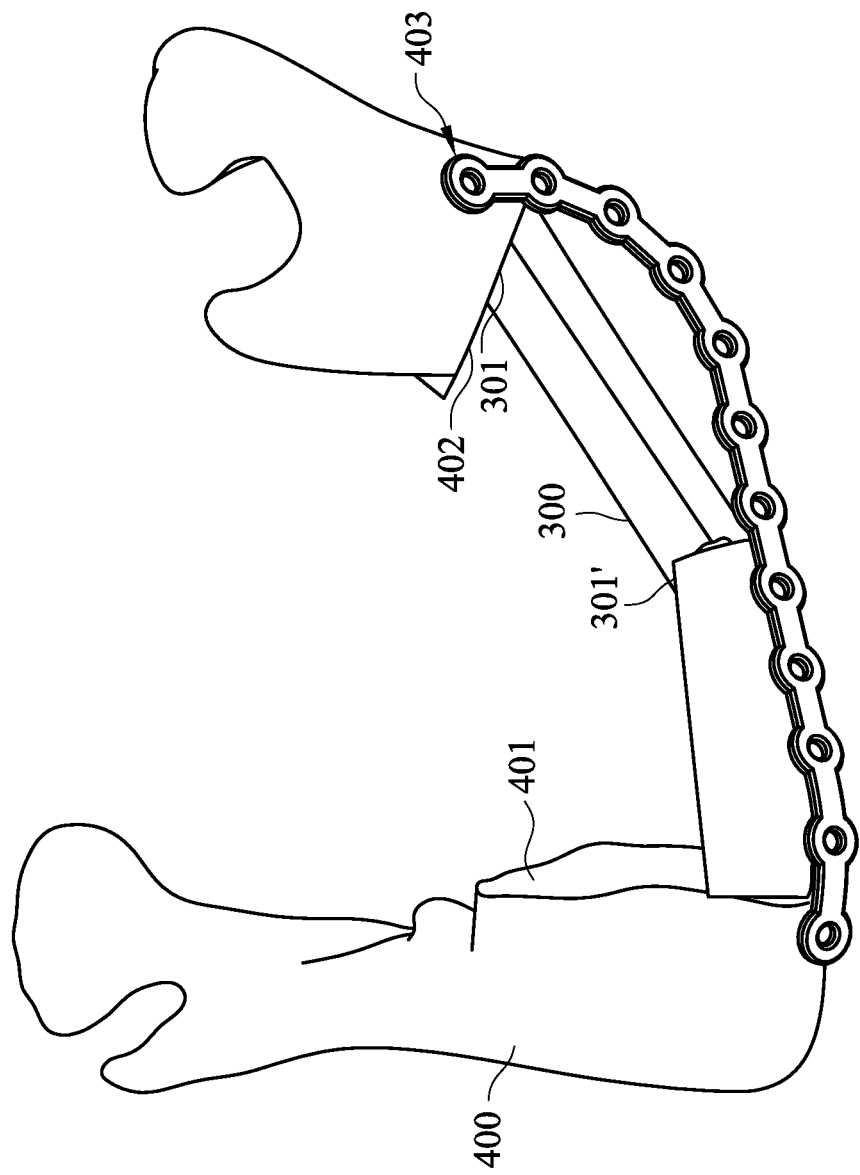
FIG. 10 is a schematic view illustrating completion of the operation according to an embodiment of the present invention.

As shown in FIG. 9 and FIG. 10, the measuring and guiding device 100 for reconstruction surgery is then used to guide cutting of the operating site (e.g., the fibula 300), with cutting planes 301, 301' being identical to the planes of the guiding portions 133, 133', The two fibulae 300 cut out through this guiding method can fit the defective site 400 of the mandible precisely.

The measuring and guiding device 100 for reconstruction surgery can measure the size of the defective site 400 of the mandible and further guide cutting of the fibula 300 of a length suitable for reconstructing the defective site 400. As has been verified by clinical tests, the measuring and guiding device 100 for reconstruction surgery can solve the problems with the current reconstruction methods that rely on the surgeons' experience, and significantly improve the perfection and the success rate of the mandible reconstruction. Additionally, the measuring and guiding device 100 for reconstruction surgery can be disassembled easily and can be reused for any patients, thereby reducing the operation cost.

The features of the present invention are disclosed above by the preferred embodiments to allow persons skilled in the art to gain insight into the contents of the present invention and implement the present invention accordingly. The preferred embodiments of the present invention should not be interpreted as restrictive of the scope of the present invention. Hence, all equivalent modifications or amendments made to the aforesaid embodiments should fall within the scope of the appended claims.

What is claimed is:

1. A measuring and guiding device, comprising:
a pair of rotary arms, each of the rotary arms comprising: a first shaft, having a first end portion and a second end portion; a first joint body, being disposed at the first end portion; and a second joint body, being disposed at the second end portion, wherein the second joint body includes a spherical hollow space;
a connector, comprising an upper joint body and a lower joint body, extending through each of the first joint bodies and connecting the pair of rotary arms together such that the pair of rotary arms are angularly adjustable relative to each other; and
a pair of fixators, each of the fixators comprising: a second shaft, having a third end portion and a fourth end portion; a third joint body, being disposed at the third end portion and joined with one of the second joint bodies with an included angle being adjustable; and a guiding portion, being disposed at the fourth end portion, wherein the third joint body is of a spherical form, wherein
the first joint bodies, the second joint bodies and third joint bodies are configured to cooperatively adjust at least one of an angle of and a distance between the guiding portions,
each of the second joint bodies are connectable to a corresponding one of the third joint bodies such that each fixators is angularly and rotatably adjustable relative to a corresponding rotary arm,
the connector is configured to fixedly fasten the pair of rotary arms relative to each other,
each of the first joint bodies is an annular structure, and surfaces of the two annular structures that contact with each other are further formed with an engaging construction respectively,
each of the first hafts further has a hollow portion which accommodates a sliding shaft piece, and the connector presses against and contacts with ends of the sliding shaft pieces so that the other end of each of the sliding shaft pieces presses against and contacts with one of the third joint bodies, and when the upper joint body and lower joint body are locked, movement between the first joint bodies and movement between each fixator and a respective rotary arm are locked simultaneously.

2. The measuring and guiding device of claim 1, wherein the engaging construction is formed with an elastic material formed thereon.

3. The measuring and guiding device of claim 1, wherein the engaging construction is a flat structure, and an elastic washer is further disposed between the two flat structures.

4. The measuring and guiding device of claim 1, wherein each of the guiding portions further has at least one first fixing guide hole formed in a side surface thereof.

5. A measuring and guiding device comprising:
  a pair of rotary arms, each of the rotary arms comprising: a first shaft, having a first end portion and a second end portion; a first joint body, being disposed at the first end portion; and a second joint body, being disposed at the second end portion, wherein the second joint body includes a spherical hollow space;
  a connector, comprising an upper joint body and a lower joint body, extending through each of the first joint bodies and connecting the pair of rotary arms together such that the pair of rotary arms are angularly adjustable relative to each other; and
  a pair of fixators, each of the fixators comprising: a second shaft, having a third end portion and a fourth end portion; a third joint body, being disposed at the third end portion and joined with one of the second joint bodies with an included angle being adjustable; and a guiding portion, being disposed at the fourth end portion, wherein the third joint body is of a spherical form, wherein the first joint bodies, the second joint bodies and the third joint bodies are configured to cooperatively adjust at least one of an angle of and a distance between the guiding portions, each of the second joint bodies are connectable to a corresponding one of the third joint bodies such that each of the fixators is angularly and rotatably adjustable relative to a corresponding rotary arm, the connector is configured to fixedly fasten the pair of rotary arms relative to each other, each of the first joint bodies is an annular structure, and surfaces of the two annular structures that contact with each other are further formed with an engaging construction respectively, each of the first shafts further has a hollow portion which accommodates a sliding shaft piece, and the connector presses against and contacts with ends of the sliding shaft pieces so that the other end of each of the sliding shaft pieces presses against and contacts with one of the third joint bodies, and when the upper joint body and lower joint body are locked, movement between the first joint bodies and movement between each fixator and a respective rotary arm are locked simultaneously, each of the guiding portions is an L-shaped plate, and inner sides of the L-shaped plate that form an included angle are formed with one of a sawtooth structure, a tine structure, or a skidproof structure.

6. The measuring and guiding device of claim 5, wherein the L-shaped plate further has at least one fixing guide hole formed in a side surface thereof.

\* \* \* \* \*